United States Patent
Hasserodt (10) Patent No.: US 9,593,362 B2
(45) Date of Patent: Mar. 14, 2017

(54) FLUOROGENIC GLYCOSIDASE SUBSTRATE AND ASSOCIATED DETECTION METHOD

(71) Applicants: ECOLE NORMALE SUPERIEURE DE LYON, Lyon (FR); UNIVERSITE CLAUDE BERNARD LYON I, Villeurbanne (FR); CENTRE NATIONAL DE LA RECHERCHE SCIENTIFIQUE, Paris (FR)

(72) Inventor: Jens Hasserodt, Lyon (FR)

(73) Assignees: ECOLE NORMALE SUPERIEURE DE LYON, Lyons (FR); UNIVERSITE CLAUDE BERNARD LYON I, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 130 days.

(21) Appl. No.: 14/417,989

(22) PCT Filed: Jul. 31, 2013

(86) PCT No.: PCT/FR2013/051855
§ 371 (c)(1),
(2) Date: Jan. 28, 2015

(87) PCT Pub. No.: WO2014/020285
PCT Pub. Date: Feb. 6, 2014

(65) Prior Publication Data
US 2015/0299762 A1    Oct. 22, 2015

(30) Foreign Application Priority Data
Aug. 2, 2012 (FR) ..................... 12 57515

(51) Int. Cl.
*C12Q 1/40* (2006.01)
*C07H 15/26* (2006.01)
*C12Q 1/34* (2006.01)

(52) U.S. Cl.
CPC .............. *C12Q 1/40* (2013.01); *C07H 15/26* (2013.01); *C12Q 1/34* (2013.01); *G01N 2333/924* (2013.01); *G01N 2333/938* (2013.01); *G01N 2400/00* (2013.01); *G01N 2458/30* (2013.01)

(58) Field of Classification Search
CPC . C07H 15/26; C12Q 1/34; C12Q 1/40; G01N 2333/924; G01N 2333/938; G01N 2400/001; G01N 2458/30
See application file for complete search history.

(56) References Cited

FOREIGN PATENT DOCUMENTS

| WO | 2008145830 A2 | 12/2008 |
| WO | 2010146164 A1 | 12/2010 |

OTHER PUBLICATIONS

Thorn-Sehold et al. Chem. Commun. (2012) 48: 6253-6255.*
International Search Report mailed Apr. 10, 2013, corresponding to International Patent Application PCT/FR2013/051855.
Fengtian Xue et al. :"Kinetic delay of cyclization/elimination-coupled enzyme assays: Analysis and solution", Bioorganic & Medicinal Chemistry Letters, vol. 21, No. 3, 2011, pp. 1069-1071.
Franciscus M. H. De Groot et al. :"Elongated multiple electronic cascade and cyclization spacer systems in activatible anticancer prodrugs for enhanced drug release", Journal of Organic Chemistry, vol. 66, 2001, pp. 8815-8830.

* cited by examiner

*Primary Examiner* — Susan Hanley
(74) *Attorney, Agent, or Firm* — Ladas & Parry LLP (57) ABSTRACT

The invention concerns novel glycosidase substrates of formula (I):

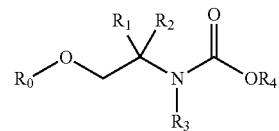

where $R_0$, $R_1$, $R_2$, $R_3$, and $R_4$ are such as defined in claim 1;
and a method for detecting the presence of a catalytically active glycosidase using one of these substrates.

16 Claims, 2 Drawing Sheets

FLUOROGENIC GLYCOSIDASE SUBSTRATE AND ASSOCIATED DETECTION METHOD

This application is a 371 of PCT/FR2013/051855, filed on Jul. 31, 2013, which claims priority to French Application No. 1257515, filed Aug. 2, 2012.

The invention relates to the technical field of probes for the detection of enzymatic activity of glycosidase type. In particular, the invention concerns novel fluorogenic substrates to detect the presence of a catalytically active glycosidase and a detection method using such substrates.

BACKGROUND OF THE INVENTION

When analysing a biological or chemical sample, the detection of glycosidase activity may be most useful (Boonacker E. and Van Noorden C. J. F. (2001) *J. Histochem. Cytochem.* 49, 1473-1486; Perry, J. D., James, A. L., Morris, K. A., Oliver, M., Chilvers, K. F., Reed, R. H., & Gould, F. K. (2006). Evaluation of novel fluorogenic substrates for the detection of glycosidases in *Escherichia coli* and enterococci. *Journal of Applied Microbiology,* 101(5), 977-985; Orenga, S., James, A. L., Manafi, M., Perry, J. D., & Pincus, D. H. (2009). Enzymatic substrates in microbiology. *Journal of Microbiological Methods,* 79(2), 139-155). Whole organisms, cells or cell extracts, biological liquids or chemical mixtures are examples of biological or chemical samples in which glycosidase activity can be detected. Glycosidases form a vast family of enzymes including numerous biomarkers of various pathologies. They are also involved in numerous benign cell processes and are the subject of countless research work by cell biologists. The detection thereof may therefore afford information on a particular metabolic or morbid condition for example.

On this account, a probe capable of detecting glycosidase activity would be most useful. The detection of this activity by capturing fluorescence light is a much more sensitive technique than collecting remaining white light after mere absorption by a probe i.e. the detection threshold is much lower. The detection of fluorescence emission is very easy to carry out which means that fluorescent probes are tools of great interest for life sciences. For example, the class of fluorophores leading to Excited State Intramolecular Proton Transfer (ESIPT) is described in particular in a) Ormson, S. M., et al. Progress in Reaction Kinetics (1994) 19, 45-91; b) Legourrierec, D., et al. Progress in Reaction Kinetics (1994), 19, 211-275; et c) Zhao, J., Ji, S., Chen, Y., Guo, H., & Yang, P. (2012). Excited state intramolecular proton transfer (ESIPT): from principal photophysics to the development of new chromophores and applications in fluorescent molecular probes and luminescent materials. *Physical chemistry chemical physics,* 14(25), 8803). The first interpretation of high fluorescence found in some phenolic compounds as being an ESIPT phenomenon can be attributed to Weller (for methyl salicylate: Weller, A. (1961). Fast Reactions of Excited Molecules. Progress in Reaction Kinetics and Mechanism 1, 187), and to Heller and Williams (for hydroxyphenylbenzoxazoles: Heller A., and Williams, D. L., J. Phys. Chem. (1970)74, 4473-4480).

The ESIPT class of fluorophores is particularly appealing for researchers in life sciences on account of its exceptional properties compared with conventional fluorophores. The exceptional properties of ESIPT fluorophores are:

(a) large Stokes shift often exceeding 130 nm and capable of reaching values of 250 nm, thereby allowing choices of instruments maximizing detection sensitivity;

(b) excellent resistance to photobleaching with rates possibly having higher orders of magnitude than those of standard fluorophores such as fluorescein;

(c) the possibility of designing fluorophores which emit brilliant fluorescence in the solid state, a rare property among all known fluorophores. This latter capability allows a signal of high intensity to be produced at the probe activation site, with minimal dilution due to scattering; and finally (d) the possibility of designing ESIPT fluorophores which emit in the red or near infrared (600 to 850 nm) where tissue transparency is highest; the corresponding probe would then be particularly suitable for imaging in living animals.

Most of these properties, if such fluorophore were to be integrated in a probe, would make a major contribution compared with the properties of conventional commercially available probes the action of which is hindered by small Stokes shifts and medium to high photobleaching, inevitably leading to fluorophores in solution state.

In the invention, the inventor focused on the judicious choice of a repeat unit cleavable by a glycosidase enzyme which would impart the complete probe, incorporating an ESIPT fluorophore as described above, with total water-solubility a prerequisite in order to reach the sites and tissues of interest. Said probe would allow a significant increase in detection sensitivity, which on this account would allow a reduction in dose and thereby would be particularly suitable for application to in vivo imaging whilst reducing toxicity problems. The level of sensitivity is closely related to: (i) photobleaching rate, (ii) the extent of accumulation of the fluorescent signal at its production site (and hence the rate of scattering from this site, and the issue of knowing whether or not the fluorophore precipitates,) (iii) the true off/on mode for probe functioning (no background noise due to non-converted fluorescence of the probe and (iv) the extent of superimposition of the excitation spectrum and emission spectrum (their separation at the baseline being the most favourable configuration; see point (a) above). Point (iv) is of particular importance since complete separation at the baseline provides the opportunity of selecting very wide filters for the light source (to excite the molecule at every possible wavelength), but more importantly for the detector (to collect photons derived from all the wavelengths emitted by the fluorophore). Point (iv) also minimises perturbation of the detection process by tissue autofluorescence (characterized by the small Stokes shift of natural fluorophores), a recurrent problem encountered with known fluorophores which also have a small Stokes shift.

In the recent years there has been increasing interest in the development of three-component initiator/spacer/fluorophore enzyme substrates, using self-immolative spacers as linkers. The important class of ESIPT fluorophores includes dichloro-HPQ (6-chloro-2-(5-chloro-2-hydroxyphenyl)-4 (3H)-Quinazolinone; CAS number: 28683-92-3) that is of particular interest since it is fully insoluble in aqueous/physiological media whilst being highly fluorescent in the solid state and only in the solid state. Nonetheless, it is very difficult to use dichloro-HPQ when developing a molecular probe to provide data on the activity of a glycosidase. In addition, the chief activities for which an HPQ-based probe has already been developed (and marketed) are those of phosphatases, due to the fact that it is impossible to create stable HPQ-based probes with a glycosylated phenolic hydroxyl since the resulting product has a propensity for rapid spontaneous hydrolysis which evidently releases free insoluble dichloro-HPQ thereby producing an erroneous signal ("background signal"). It is also to be noted that the marketing by Molecular Probes of such glycosylated compounds (ELF 97 glucuronidase substrate (No. E6587) and ELF 97 chitinase/N-acetylglucosaminidase substrate (No. E22011) was interrupted in 2008 and the study thereof by some researchers has not been continued (a) Chen, K.-C., Wu, C.-H., Chang, C.-Y., Lu, W.-C., Tseng, Q., Prijovich, Z. M., Schechinger, W., et al. (2008). Directed Evolution of a Lysosomal Enzyme with Enhanced Activity at Neutral pH by Mammalian Cell-Surface Display. *Chemistry & Biology*, 15(12), 1277-1286; b) Štrojsová, A., & Dyhrman, S. T. (2008). Cell-specific β-N-acetylglucosaminidase activity in cultures and field populations of eukaryotic marine phytoplankton. *FEMS Microbiology Ecology*, 64(3), 351-361). The reason relates to the intrinsic hydrolysis instability of phenolic glycosides and in particular those constructed from electron-depleted phenols, such as dichloro-HPQ. It is effectively known that any nitrophenol-based glycoside (a phenol having the same electron depletion as dichloro-HPQ) hydrolyses spontaneously at physiological pH. It is also known that this stability problem is severely aggravated at more acid pH values (e.g. at a pH of 6.5), compared with physiological pH (pH 7.4).

Solutions leading to greater even complete absence of spontaneous degradation of the probes and hence of the production of erroneous signals, a fundamental prerequisite for use thereof for in vitro and in vivo applications, have been put forward involving the construction of a three-component probe. These comprise a para-hydroxy-or para-amino-benzyl spacer grafted on the phenolic fluorophore (WO2008145830). Although such para-hydroxybenzyl spacers have already been used in the development of prodrugs since the early 1980s (Wakselman, M. New Journal of Chemistry (1983), 7, 439-447), they have a recognized major drawback: the use of para-hydroxybenzyl spacers in artificial enzyme substrates leads to permanent alkylation of the protein, often in the vicinity of or inside the catalytic site. This negative property was subsequently put to advantage in numerous articles which proposed enzyme-inactivating substrates i.e. leading to an enzyme which is no longer capable of converting the substrate molecules (Zhu, J.; Withers, S. G.; Reichardt, P. B.; Treadwell, E.; Clausen, T. P. *Biochem. J.* 1998, 332, 367-371), as shown in following Scheme 1.

The different studies on enzymatic labelling by ortho- or para-hydroxybenzyl enzyme substrates show that quinone methides are highly reactive species which alkylate the nucleophiles and risk randomly modifying the molecular properties of the biomacromolecules lying in their immediate vicinity. The reduced activation or catalytic capabilities of the target enzyme are evidently most harmful for the sensitivity of imaging experiments using a said fluorogenic probe since enzymatic amplification is lost. Aside from the direct inactivation of the target enzyme, random alkylation of the surface of this protein or of any other neighbouring protein present also carries the risk of an immune response. Both cases generate limited tolerance by the respective body hence subjecting it to high toxicity (Grinda M. et al. ChemMedChem 2011, 6, 2137-2141)

BRIEF SUMMARY OF THE INVENTION

Within this context the Applicant has set out to provide other spacers 1) which would allow the forming of a stable probe incorporating an ESIPT fluorophore, hence with minimised background fluorescence of the non-converted probe, and 2) which does not exhibit the same risks in terms of toxicity as the hydroxybenzyl spacer described in the state of the art.

It is the objective of the invention to propose novel glycosidase substrates which are stable in an aqueous medium and which remain non-fluorescent or scarcely fluorescent at a much different wavelength than the wavelength at which the released fluorophore is fluorescent, but which react with glycosidases to produce a small fluorescent molecule corresponding to an ESIPT fluorophore such as dichloro-HPQ. According to the invention, it is envisaged to propose a glycosidase substrate having the following properties:

- the possible obtaining of specificity for a particular glycosidase in relation to the choice of glycosyl group on the probe;
- no background fluorescence since there is no spontaneous degradation of the probe;
- good conversion kinetics under the action of the target glycosidase;
- greater biocompatibility than probes using hydroxybenzyl spacers having recognized toxicity.

More specifically the invention concerns compounds of formula (I):

Scheme 1

Z = leaving group; Nu: nucleophile on enzyme where:
R$_0$ is a glycosyl group bonded via its anomeric carbon to the remainder of the molecule;
R$_1$, R$_2$ and R$_3$ are defined as follows:
either R$_1$ is a (C$_1$-C$_4$)alkyl or hydrogen atom, R$_2$ is a (C$_1$-C$_4$)alkyl and R$_3$ is a (C$_1$-C$_4$)alkyl;
or R$_1$ is a (C$_1$-C$_4$)alkyl or hydrogen atom and R$_2$ and R$_3$ are linked and, together with the carbon and nitrogen atoms to which they are bonded, they form an aliphatic heterocycle, this heterocycle possibly being substituted by a group of ammonium, carboxylate or sulfonate type, allowing increased water-solubility of the substrate;
or R$_3$ is a (C$_1$-C$_4$)alkyl and R$_1$ and R$_2$ are linked and, together with the carbon atom to which they are bonded, form an aliphatic carbocycle;
R$_4$ is such that R$_4$OH belongs to the class of fluorophores leading to excited state intramolecular proton transfer known as ESIPTs, in the form of a mixtures of optical isomers in any proportion, or in a form enriched with an optical isomer.

The compounds of the invention, in relation to the selected glycosyl group, act as a molecular probe capable of identifying the presence of specific glycosidase enzymatic activity via fluorescence detection. The R$_0$—O bond is able to be cleaved via hydrolysis in the presence of a glycosidase enzyme acting as catalyst of the cleavage reaction.

More specifically, the probe is invisible before meeting the targeted glycosidase enzyme (i.e. "stealth probe"), but when it is chemically modified by the said enzyme it is fragmented via a cascade reaction to produce intense fluorescence. The probe is composed of three molecular components: i) an intelligent spacer, —OCH$_2$C(R$_1$R$_2$)N(R$_3$)C(O)— which at one end carries ii) a glycosyl group acting as substrate for the target enzyme, and at the other end iii) an OR$_4$ group which when it is released in its hydroxylated form by said fragmentation, belongs to the ESIPT class of fluorophores.

To overcome the unfavourable conversion kinetics associated with a hydroxyethylcarbamate spacer carrying a primary hydroxy group at distal position relative to the tertiary carbamate group, the present invention proposes a novel family of spacers of hydroxy-amine type which are substituted such that they are pre-organised for cyclisation to a cyclic carbamate. This pre-organisation accelerates the conversion process during activation by an enzyme.

With this particular choice of spacers it is possible to obtain two fundamental properties for the corresponding molecular probe: (a) it makes the probe insensitive to spontaneous degradation and hence to producing a false positive fluorescent signal, and (b) it guarantees rapid fragmentation kinetics during conversion by the target enzyme to obtain performance adapted to applications in the field of life sciences. The R$_0$ group is capable of being cleaved from the remainder of the molecule through the action of the target glycosidase, which leads to an unstable intermediate spontaneously and rapidly immolated by cyclisation/cleavage reaction to release a fluorescent precipitate and thereby produce a fluorescent signal.

The present invention therefore concerns formula (I) compounds irrespective of their variant of embodiment described in the present patent application, for in vivo detection in man or animal of a glycosidase enzyme.

According to another aspect, the invention concerns an in vitro method to detect the presence of a catalytically active glycosidase enzyme, by means of a formula (I) compound according to the invention. More specifically, the invention concerns a method to detect the presence of a catalytically active glycosidase enzyme comprising the steps of:
contacting a sample suspected of containing the said glycosidase with a formula (I) compound of the invention;
applying suitable conditions to allow the formation of a fluorescent, compound in particular in the form of a precipitate, by cleaving the covalent bond between —O—R$_0$, followed by cleavage of the —C(O)—OR$_4$ bond after cyclisation of the spacer —OCH$_2$C(R$_1$R$_2$)N(R$_3$)C(O)—; and
quantitative or qualitative analysis of the said fluorescent precipitate.

The precipitate which can be obtained from the formula (I) compounds of the invention, by cleaving the covalent bond between O and R$_0$ followed by cleavage of the —C(O)—OR$_4$ bond after cyclisation of the spacer —OCH$_2$C(R$_1$R$_2$)N(R$_3$)C(O)—, is highly fluorescent, whereas the corresponding formula (I) compound is scarcely or not at all fluorescent. The compounds of the invention which are glycosidase enzyme substrates behave as probes functioning in off/on mode.

In particular, the detection method of the invention can be implemented under physiological conditions, in particular in an aqueous medium buffered at a pH in the order of 7.4.

In one embodiment of the invention, the analysis of the fluorescent compound or precipitate comprises the following steps:
exposing the fluorescent precipitate to a light source capable of producing light at an absorption wavelength of the fluorescent precipitate; and
detecting the resulting fluorescence of the precipitate.

BRIEF DESCRIPTION OF THE DRAWINGS

FIG. 3 evidences the capacity of probe I.1 to cross the cell membrane, to enter into contact with the target enzyme b-gal located in the cytoplasm, and to be converted by the enzyme.

DETAILED DESCRIPTION OF THE INVENTION

A more detailed description is now given of the invention. Beforehand some terms used for the formula (I) compounds are defined below.

By <<alkyl>> is meant a saturated hydrocarbon chain which may be straight-chain or branched. Preferably the term alkyl, unless otherwise specified, designates an alkyl group comprising 1 to 12 carbon atoms and preferably 1 to 6 carbon atoms, in particular a ($C_1$-$C_4$)alkyl group. Methyl, ethyl, n-propyl, isopropyl, iso-butyl and tert-butyl are examples of ($C_1$-$C_4$)alkyl groups (alkyl having 1 to 4 carbon atoms).

By <<aryl>> is meant an unsaturated, hydrocarbon mono-, bi- or polycyclic ring, preferably having 5 to 20 members, preferably 5 to 15 members, and comprising at least one aromatic ring alternating single bonds and double bonds. As examples of an aryl group mention can be made of the phenyl, naphthyl, anthrancenyl, phenanthrenyl and cinnamyl groups. The term aryl also includes said unsaturated, hydrocarbon mono-, bi- or polycyclic rings in which one of the constituent carbons is in —C(O)-carboxy form such as 1H-phenalene-1-one (CAS no. 548-39-0).

By <<heteroaryl>> group is meant a mono-, bi- or polycyclic carbocycle, preferably comprising 6 to 20 members, more preferably 6 to 15 members and comprising at least one aromatic group and at least one heteroatom selected from among oxygen, nitrogen or sulfur atoms integrated within the carbocycle. As examples of a heteroaryl group the following can be cited: 2-, 3- or 4-pyridinyl, 2- or 3-furoyl, 2- or 3-thiophenyl, pyrrolyl, imidazolyl, pyrazolyl, thiazolyl, benzothiazolyl, oxazolyl, benzoxazolyl, isoxazolyl, pyridinyl, pyrazinyl, pyrimidinyl, tetrazolyl, thiadiazolyl, oxadiazolyl, triazolyl, pyridazinyl, indolyl, oxanyl, 4(1H)-quinolinonyl, dibenzothiophenyl, dibenzofuranyl and 9H-carbazolyl. The term heteroaryl also includes the said groups in which one of the constituent carbons is in —C(O)— carboxy form such as 4(3H)-pyrimidinonyl or 4(3H)-quinazolinonyl.

When it is indicated that a group is substituted, this means that it is substituted by one or more substituents selected in particular from among chlorine, bromine, iodine or fluorine atoms, the groups: cyano, alkyl, trifluoroalkyl, trifluoromethyl, alkenyl, alkynyl, cycloalkyl, aryl, heteroaryl, heterocycloalkyl, amino, alkylamino, dialkylamino, hydroxy, alkoxy, aryloxy, alkoxycarbonyl, aryloxycarbonyl, the said groups themselves possibly being substituted. The terms used to define these substituents are those usually recognised by persons skilled in the art.

By <<glycosidase>> is meant a glycoside hydrolase enzyme which has the capability of catalysing the hydrolysis of glycoside bonds, to release at least one oside compound.

Par <<glycosyl>> group is meant any mono- or polysaccharide sugar bonded to the remainder of the molecule by a glycosyl bond i.e. via its anomeric carbon giving rise to an O/O-acetal. The anomeric carbon may adopt an alpha or beta configuration. As an example of an $R_O$ group mention can be made of the mono-glycosyl groups i.e. formed of a single saccharide unit, and polyglycosyl groups i.e. formed of several saccharide units the same or different. The saccharide units may in particular be of hexose or pentose type, and selected from among galactose, glucose, mannose, gulose, allose, altrose, idose, talose, fucose, fructose, arabinose, lyxose, ribose and xylose for example. The saccharide units may have L or D stereochemistry. All the possible glycosyl groups forming glycosidase substrates can be used as $R_O$. The glycosyl units may or may not be functionalised, in particular with an acetyl or amino group. N-acetyl-hexosamines are examples of a glycosyl group. Most often, the $R_O$ group comprises 1 to 50 saccharide units. For a polyglycosyl it may be a homopolymer or copolymer having random, alternate or block structure.

The $R_O$ groups have the characteristic of being able to be cleaved from the remainder of the molecule under the action of a glycosidase enzyme. The enzyme acts as catalyst of the cleavage between $R_O$ and the oxygen atom to which it is bonded. Said cleavage may be the consequence of hydrolysis in an aqueous medium for which the glycosidase enzyme acts as catalyst. This is why the said glycosidase enzyme is said to be catalytically active. Examples of such $R_O$ groups behaving as glycosidase substrates are given below: the mono-glycosyl groups selected from among galactosyl, glucosyl, mannosyl, gulosyl, allosyl, altrosyl, idosyl, talosyl, fucosyl, fructosyl, arabinosyl, lyxosyl, ribosyl, xylosyl, glucuronyl and N-acetyl-hexosaminyl, and the polyglycosyl groups formed of these monoglycosyl groups whether the same or different.

The $R_O$ group is preferably chosen to be specific to a glycosidase of interest. On the other hand, some glycosidases have the capability of cleaving a set of different $R_O$ groups; among these mention can be made of hexosaminidase.

As examples of glycosidase enzymes which can be targeted by the fluorogenic probes of the invention mention is made of the following: N-acetyl-β-galactosaminidase; N-acetyl-β-glucosaminidase; α-amylase; α-arabinofuranosidase; α-arabinosidas; β-cellobiosidase; β-chitobiosidase; α-galactosidase; β-galactosidase; α-glucosidase; β-glucosidase; β-glucuronidase; α-maltosidase; α-mannosidase; β-mannosidase; β-xylosidase; β-D-fucosidase; α-L-fucosidase; β-L-fucosidase; L-iduronidase and cellulase (Orenga, S., James, A. L., Manafi, M., Perry, J. D., & Pincus, D. H. (2009). Enzymatic substrates in microbiology. *Journal of Microbiological Methods*, 79(2), 139-155).

<<Fluorescence>> is the property whereby a molecule excited by light of a given wavelength emits light at a longer wavelength. Fluorescence is a phenomenon resulting from the interaction between a fluorophore and an incident photon. This process is called excitation. The absorption of the photon causes an electron in the fluorophore to change over from its fundamental state to a higher energy level. The electron then returns to its original level emitting a photon. This process is called fluorescence emission. The fluorophore then emits light at a longer wavelength than that of the absorbed photon. This is simply due to the fact that the energy of the emitted photon is lower than the energy of the absorbed photon on account of energy dissipation during the lifetime of the excited state. This definition is given in patent application WO 2004/058787.

The compounds (I) of the invention are called <<glycosidase substrates>> since they are converted to another substance during a chemical reaction, hydrolysis in particular, catalysed by a glycosidase. During said reaction, the compounds (I) (also called <<probes>>) are cleaved by action of the target glycosidase, which leads to the formation of a fluorescent precipitate and of a non-fluorescent product.

The OR$_4$ group is selected so that the fluorescent precipitate obtained which corresponds to R$_4$OH is an ESIPT fluorophore. Examples of such OR$_4$ groups meet formula (C):

(C)

where:
either X$_2$ is an oxygen atom and X$_1$ is a group from among —NH$_2$, —OH, —SH, alkyl, aryl, —O-alkyl, —O-phenyl, —NH-alkyl, —NH-phenyl, —S-alkyl or —S-aryl, the said alkyl and phenyl groups possibly being substituted or unsubstituted;
or X$_2$ is a nitrogen atom and is bonded to X$_1$ which then represents CH, O, S, N or NH to form a heteroaryl, substituted or unsubstituted;
and represents an aryl or heteroaryl, substituted or unsubstituted, selected for example from among the phenyl, naphthyl groups, and:

the said groups possibly being substituted or unsubstituted, with X$_3$ representing S, O or NR", and R" representing a hydrogen atom or (C$_1$-C$_4$)alkyl group.

The ESIPT fluorophores display a Stokes shift which exceeds 100 nm and often reaches 200 nm. All ESIPT fluorophores lose this fluorescence emission corresponding to a Stokes shift higher than 100 nm, if their phenolic-type OH group is alkylated, acylated or otherwise functionalised, which prevents transfer of a hydrogen atom to the heteroatom X$_2$ in the illustration given with formula (C), during excitation via irradiation, and thereby prevents the emission of fluorescence characteristic of the proton transfer process.

Most often, the R$_4$ group corresponds to a phenyl group which is unsubstituted or substituted and/or is fused with one or more unsaturated carbocycles optionally comprising a heteroatom such as nitrogen. This phenoxy derivative OR$_4$, when not linked to the substrate, corresponds in its protonated form to a phenolic derivative HO—R$_4$ which belongs to the ESIPT class of fluorophores.

OR$_4$ derivatives of phenoxy type correspond for to the following preferred structures (A) or (B) for example:

(A)

where:
T is —NH—C(O)—, —S—, —O—, —NH, N-alkyl or N-aryl;

Ra is hydrogen or an electron-attractor carbon substituent such as —CN or —COORd with Rd representing a (C$_1$-C$_4$)alkyl group, or else Ra is —CONReRf, with Re and Rf the same or different and representing hydrogen or (C$_1$-C$_4$)alkyl group, or else Ra is —CF$_3$ or a group from among 2-oxazolyl, 2-thiazolyl, 2-imidazolyl, 2-benzoimidazolyl, 4-pyrimidinon-2-yl or quinazolinon-2-yl;

Rb is hydrogen, a chlorine, bromine, iodine or fluorine atom, —OH, —NH$_2$, —NRgRh, —NHRg or —ORg, with Rg and Rh each independently representing a (C$_1$-C$_4$)alkyl;

or else Ra and Rb and linked together to form a hydrocarbon chain comprising 4 or 5 members, saturated or unsaturated, substituted or unsubstituted, optionally interrupted by one or more heteroatoms selected from among N, S and O;

Rc is hydrogen, Br, Cl, I or F;

(B)

where:
T' is NH$_2$, OH, an aryl group, (C$_1$-C$_4$)alkyl group, SH, NHR, OR, NRR' or SR, with R and R' the same or different representing a (C$_1$-C$_4$)alkyl or aryl group;

R'a is hydrogen or an electron-attractor carbon substituent such as —CN, or —COOR'd where R'd represents a (C$_1$-C$_4$)alkyl group, or R'a is —CONR'eR'f with R'e and R'f the same or different representing hydrogen or a (C$_1$-C$_4$)alkyl group, or else R'a is —CF$_3$ or 2-oxazolyl, 2-thiazolyl, 2-imidazolyl, 2-benzoimidazolyl, 4-pyrimidinon-2-yl or quinazolinon-2-yl;

R'b is hydrogen, a chorine, bromine, iodine or fluorine atom, —OH, —NH$_2$, —NR'gR'h or —OR'g, with R'g and R'h the same or different representing a (C$_1$-C$_4$) alkyl group;

or else R'a and R'b are linked to form a hydrocarbon chain having 4 or 5 members, saturated or unsaturated, substituted or unsubstituted, optionally interrupted by one or more heteroatoms selected from among N, S and O.

When the target glycosidase has released a free primary hydroxyl group at the end opposite the acyl group of the spacer —OCH$_2$C(R$_1$R$_2$)N(R$_3$)C(O)—, this latter cyclises spontaneously thereby releasing the fluorophore HOR$_4$.

In one particular embodiment, the glycosidase substrate of the invention is of formula (IA):

(IA)

where R$_0$, R$_1$, R$_2$ et R$_3$ are such as defined for compounds (I).

In one preferred embodiment of substrates (I) and (IA) according to the invention, R$_1$=H and R$_2$ et R$_3$ are linked together and form a —(CH$_2$)$_m$-chain with m=3, 4 or 5. In such case, the kinetics of hydrolysis and cyclisation under the action of a glycosidase enzyme are particularly satisfactory.

In another embodiment of substrates (I) and (IA) according to the invention R$_1$, R$_2$ et R$_3$, the same or different, are a (C$_1$-C$_4$)alkyl, e.g. a methyl or ethyl. For example R$_1$=R$_2$=R$_3$=—CH$_3$.

These two manners of pre-organising the spacer —OCH$_2$C(R$_1$R$_2$)N(R$_3$)C(O)— for cyclisation to a cyclic carbamate, consisting either of inserting two alkyl substituents to the alpha carbon of the carbamate group, or of including the bond between the nitrogen of the carbamate group and its alpha carbon in a heterocycle, accelerate the immolation process. The bond between the nitrogen of the carbamate group and its alpha carbon is inserted for example in a heterocycle belonging to the class of pyrrolidines (5-membered) or to the class piperidines (6-membered), which allows further improvement in the conversion kinetics catalysed by the glycosidases.

Scheme 4 below shows an example of a fluorogenic substrate (Example I.1) in the case when R$_2$ and R$_3$ are linked and form a —(CH$_2$)$_m$— chain where m=4, and the reaction cascades causing its fragmentation after initiation due to cleavage by the target glycosidase.

Scheme 4

ESIPT: ✻ ON ✻
intense fluorescence
Em(max) = 520 nm (green-yellow)
total insolubility
minimum photobleaching
exceptional Stokes shift The following substrates I.1 to I.4 represent four examples of the invention when $R_2$ and $R_3$ are linked and form a —$(CH_2)_m$— chain where m=3 or 4.

Examples I.1 to I.4 comprise the conventional ESIPT fluorophore dichloro-HPQ. However, this invention is applicable to all $R_4$ substituents allowing an ESIPT phenomenon to be obtained, since the chemistry for suppression of ESIPT fluorescence is the same and simple: the incorporation of the hydroxyl of the fluorophore in the carbamate group prevents the formation of the internal hydrogen bond. For the preparation of derivatives of dicloro-HPQ, reference can be made to EP 0641 351 or WO 2004/058787, for example.

Some examples of ESIPT phenolic fluorophores which can be used in the invention and which are described in the literature, with specification of their excitation and emission maxima and quantum yield ("QY") are listed below.

101 fluorescence (MeCN)
370 (Exc)/570 (Em)
QY: 0.20

102

"brilliant blue fluorescence" (H₂O)
360 (Exc)/516 (Em)
QY: 0.60

103a X = O, no published brilliance or QY
Exc: 360; Em(max): 670 nm
103b X = NH, 300/600

104

"intense green fluorescence"

105 in 3-methyl-pentane:
Exc (max): 385 nm
Em (max): 550 nm
QY: 0.50

106

X = O
Ex/Em 429/596 nm
QY: 0.15
X = S
Ex/Em 442/636 nm
QY: 0.25

107 solid state (QY = 0.47) in
solution (QY = 0.40, CHCl₃),
(EM = 466 nm).

108

(excited at 350 nm in toluene)
X = O Em(max): 545 nm QY 0.40
X = S Em(max): 565 nm QY 0.36
X = NEt Em(max): 600 nm QY 0.21

109

(excited at 300 nm in solid state)
X = S 517 nm (Em) QY 0.30
X = O 506 nm (Em) QY 0.42
X = NH 462 nm (Em) QY 0.035

101: Stefani, V., et al. Dyes and Pigments (1992)20, 97-107.

102: Yamada, S., et al. Chemistry Letters (1999), 197-198.

103a: Nagaoka, S., et al. Journal of Photochemistry and Photobiology a—Chemistry (1999)122, 151-159.

103b: Douhal, A., et al. Chemical Physics Letters (1994) 217, 619-625.

104: Kemp, D. S., et aZ, Journal of Organic Chemistry (1981)46, 1804-1807.

105: Mordzinski, A., et al. Journal of Physical Chemistry (1986)90, 1455-1458.

106: Lins, G. O. W., et al. Dyes and Pigments (2010)84, 114-120.

107: Seo, J., et al Journal of Photochemistry and Photobiology a—Chemistry (2007)191, 51-58.

108: Kauffman, J. M., et al. Journal of Heterocyclic Chemistry (1995)32, 1541-1555.

109: Heller, A., et al. J. Phys. Chem. (1970)74, 4473-4480.

110: JP2004142131.

Therefore the $R_4$ group can be selected so that the glycosidase substrate releases a fluorophore selected from among the phenolic ESIPT fluorophores 101, 102, 103a, 103b, 104, 105, 106, 107, 108, 109 and 110, after cleavage by the target glycosidase. Other examples of ESIPT fluorophores able to correspond to $HOR_4$ are given in the publications: Prog. Recation Kinetics Vol 19, 1994, 45-91; Adv. Mater. 23, 2011, 3615-3642; Phys. Chem. Chem. Phys., 2012, 14, 8803-8817, Prog. Reaction Kinetics, Vol. 19, 1994, 211-275, to which reference can be made for further details.

The substrates (I) of the invention can be obtained by coupling e.g. between a Cl—C(O)—$OR_4$ compound (with $R_4$ such as defined for the formula (I) compounds) and an amine of formula (II):

(II)

where $R_0$, $R_1$, $R_2$ and $R_3$ are such as defined for the formula (I) compounds, or an amine of formula (II'):

(II')

where $R'_0$ is a glycosyl group precursor $R_0$ when the latter comprises an amide or carboxylic acid function and $R_1$, $R_2$ et $R_3$ are such as defined for the formula (I) compounds. In particular, when the glycosyl group $R_0$ comprises an amide or carboxylic acid function, the said function can be obtained from a-OH or —$NH_2$ function respectively, using techniques well known to those skilled in the art.

The different compounds of the invention can be found in all possible forms of optical isomers, optionally in a mixture in any proportion unless otherwise specified. According to one particular embodiment, the compounds of the invention comprising an asymmetric carbon are in racemic form, the R and S forms being in substantially equal proportions.

According to another embodiment, the formula (I) compounds of the invention may be in a form enriched with a diastereoisomer or enantiomer form with diastereoisomeric or enantiomeric excess higher than 80%, even higher than 95%, even in pure isomeric form i.e. with diastereoisomeric or enantioemeric excess higher than 99%.

The compounds (I) are isolated in diastereoisomeric- or enantiomeric enriched form using conventional separation techniques: for example fractionated recrystallizations of a salt of the racemic can be used with an acid or optically active base the principle of which is well known, or, most often, conventional chiral or non-chiral phase chromatography techniques.

With the present invention the activity of the glycosidases is made accessible by fluorescence imaging using ESIPT fluorophores, e.g. of dichloro-HPQ type. No background noise due to spontaneous degradation (i.e. in the absence of target glycosidase, in physiological medium) is observed. The probe itself is not or only scarcely fluorescent, in particular at the emission wavelength of the free ESIPT fluorophore on which the detection/imaging instrument is adjusted. The probe therefore functions in off/on mode and can be used to develop analyses with maximum sensitivity. In relation to the selected $R_0$ group, the invention allows glycosidases to be targeted having high selectivity for particular glycosyl groups. This is made possible by coupling a said group at the end of the intelligent spacer —$OCH_2C(R_1R_2)N(R_3)C(O)$—.

The substrates of the present invention benefit from good permeability with respect to the cell membrane compared with other known fluorogenic enzyme substrates and will be capable of easy cell entry (to be compared with: Duhamel, S. et al. Journal of Microbiological Methods 75 (2008) 269-278), which means that these substrates can be used for different applications in a large variety of cells. In addition, the substrates of the present invention are generally soluble but scarcely fluorescent in solubilised form in water; however, they emit a highly fluorescent signal in an aqueous solution containing the substrate and the corresponding glycosidase. With dichloro-HPQ, this fluorescent signal is emitted in the solid state by the precipitate formed under the action of the glycosidase since dichloro-HPQ is highly insoluble in most solvents but in particular in aqueous media. Other ESIPT fluorophores are not particularly soluble either in aqueous media, but most maintain their capacity to emit fluorescence even if they are precipitated. The suitable in vitro conditions to allow the formation of a fluorescent precipitate during hydrolysis by a glycosidase are purely aqueous media such as a buffered or physiological medium. One important point is that the precipitate is formed during hydrolysis by a glycosidase without compromising glycosidase activity. Therefore their use for identification in biological samples or the detection of discrete bands for non-denaturing PAGE separation and Western transfer is possible. More ample details on detection conditions and techniques which can be used are given in WO 2004/058787 and EP-0641351 which can be directly applied to the present invention.

The probes of the invention attract interest for several highly sensitive applications in life sciences, and in particular: (1) high yield screening for glycosidase activity expressed by bacterial colonies on an agar plate (colony analysis); (2) in vitro detection of glycosidase in biological liquids (haematology and others); (3) visualisation of activity at a single cell in flow cytometry; (4) detection of subcellular glycosidases in cultured cells (confocal fluorescence microscopy); (5) histochemical detection of glycosidase (on tissue scale); and finally (6) in vivo imaging of a whole animal. The probes of the invention meet the requirements of experts for the development of probes having greater robustness than those currently available (National Research Council of the U.S.A. (2006) Visualizing Chemistry: The Progress and Promise of Advanced Chemical Imaging, The National Academies Press). In particular, the rapidly growing field of in vivo molecular imaging lacks intelligent stealth probes which are sufficiently robust and of limited molecular complexity so that they can be produced at limited cost (Baker, M. (2010). Whole-animal imaging: The whole picture. Nature 463, 977-980).

Therefore the compounds of formula (I) and (IA), as glycosidase substrates of the present invention, have a large number of potential applications. Examples of such applications include:

(a) the design of analyses on bacterial colonies. These are currently performed on agar plates (Petri dishes) in which up to 3 000 colonies can be distinguished without the need for their active separation in separate compartments such as the wells in multi-well plates. It is therefore possible (1) to design tests on clinical samples allowing the identification in a set of bacterial lines of a pathogenic line of interest; (2) to conduct bulk parallel tests on a bank of proteins for production thereof expressed by a conventional bacterial host (often commercially available). This collection of proteins can evidently contain a protein of particular interest e.g. a glycosidase having selectivity for a specific glycosyl group, or a glycosidase hydrolysing a non-natural glycoside bond. In the growing area of the directed application of glycosidases in general or of enzymes in particular, there is a strong demand for efficient, sensitive analyses to screen a large number of protein variants, easily exceeding $10^6$. The application of the probe of the invention can be more easily envisaged by dissolution in agar solution before microplating where it gels. Alternatively, the substrates are incubated with colonies by immersion of a filter before it is pressed onto the colonies. The main advantage contributed by the probe of the invention for said analysis on colonies is the on-site precipitation of the fluorophore; dilution of the fluorescent signal by scattering is therefore much reduced allowing longer incubation times and hence greater sensitivity for analysis. The very large Stokes shift of dichloro-HPQ (approximately 140 nm), or of any analogue of HPQ, should not be underestimated; it also contributes towards excellent sensitivity making it easily distinguishable from the native fluorescence originating from the biological sample.

(b) In vitro (histology) and in vivo imaging. Having regard to the very low solubility of free dichloro-HPQ or of any analogue of HPQ, any release thereof in a complex biological environment allows fluorescence imaging with high spatial control. Fluorescence imaging is a widely applied technique to evidence subcellular structures. The high resolution locating of specific glycosidase activity can be made possible through the use of a probe according to the invention.

On the contrary, the compounds of formula (I) and (IA) which form passive fluorescent probes (those that are not converted by an enzyme) are equipped with a ligand specific to a cell receptor (or with an antibody specific to a molecular epitope of the cell) and attach onto this receptor via non-covalent interactions; they are therefore not devoid of signal dilution effects. Above all, a receptor is equivalent at best to a fluorescent tracer. The sensitivity of analysis based on such probes is necessarily much lower than the sensitivity of an active probe which has the benefit of catalytic amplification of the signal.

The compounds of formula (I) and (IA) according to the invention can also be used for macroscopic fluorescence imaging i.e. of a whole body. If the probe enters the cell wall to reach the glycosidase activity of interest, the release of the free fluorophore excludes rapid dilution of the signal by sharing with the extracellular space. In general, this allows extended incubation times before imaging, which are particularly useful when the enzymatic activity has low level expression.

The glycosidase substrates of the invention can be prepared using known techniques detailed in the following examples. For example, a protected glycosyl group can be grafted on the spacer group. After a coupling step to insert the fluorophore via its phenolic hydroxyl, the glycosyl group can be deprotected. The complete probe thus obtained can be purified before use using conventional techniques.

The following examples illustrate the invention but are not in any way limiting.

General

Column chromatography was performed on 60-mesh silica gel (40-63 µm). The $^1$H and $^{13}$C NMR spectra were recorded at 500 MHz and 125 MHz, respectively, in deuterated chloroform. The chemical shifts (δ) are given in ppm and indicated with reference to tetramethylsilane or according to residual signals of the solvent; the abbreviations s=singlet, d=doublet, t=triplet, m=multiplet, br=broad are used. The NMR coupling constants (J) are given in Hertz. Analyses by fluorescence were carried out in black propylene plates, 96-well (Corning, Corning Inc.) or 384-well (NUNCLONE, Nunc Inc.) and recorded on a microplate fluorimeter (Mithras LB940 by Berthold Technologies). Unless otherwise specified, the chemical products were purchased with the analytical reagent quality and used without further purification.

The dry commercial DCM was dried and purified by passing through an activated alumina column under flow of argon (GT S100 Solvent Station System). The TEA was distilled from calcium hydride and stored on KOH pellets. The other dry purchased reagents were dried on molecular sieves. Unless otherwise indicated, all reactions were conducted in an air atmosphere with commercially obtained solvents and reagents, without any additional drying or purification. Millipore water was obtained from an Elga Purelab purification system and used for all experiments.

The following abbreviations are used:
TEA=triethylamine
EA=ethyl acetate
Cy=cyclohexane
DCM=dichloromethane

Example I.1

Substrate I.1 was prepared as described in following Scheme 5:

Scheme 5: Chemical Synthesis of Example I.1

-continued

I.1

Preparation of Compound 4:
(Adapted from Li C., Wang W.-T., *Tetrahedron Lett.* 2002, 43, 3217)

To a solution of β-D-Galactose pentaacetate 1 (2 g; 5.1 mmol) under argon in anhydrous DCM (14 mL) was added 2-piperidinemethanol 2 (887 mg; 7.7 mmol). The reaction mixture was then cooled to 0° C., trifluoroborate etherate (6.3 mL; 48.7 mmol) was added dropwise and this mixture was left under agitation at this temperature for one hour before being brought to 35° C. for 16 hours. This reaction mixture was divided between DCM and a saturated solution of potassium carbonate ($Na_2CO_3$). The organic phase was washed twice with saturated $Na_2CO_3$ solution and once with saturated brine. The organic phase was then acidified with aqueous $KH_2PO_4$ (10%) solution and 1 mL of HCl (1 M) to obtain a pH of about 3, and washed twice with aqueous $KH_2PO_4$ solution (10%). The combined acid aqueous phases were washed once with DCM and basified with saturated $Na_2CO_3$ solution then extracted three times with DCM. The combined basic organic phases were dried ($Na_2SO_4$), filtered and evaporated under reduced pressure to give compound 4 in the form of an orange solid (1.327 g; 58%). The NMR spectra of this compound were very complex but clearly displayed the presence of two diastereoisomers (due to commercial product 2 which was racemic) and showed that the β anomeric bond was indeed formed (coupling of the anomeric proton of 7.9 Hz, characteristic of this type of bond).

$^1$H NMR (500 MHz, $CDCl_3$) δ=5.36 (t, 1H), 5.17 (ddd, 1H), 4.99 (dd, 1H), 4.44 (2×d, J=7.9, 1H), 4.17-4.09 (m, 2H), 3.88 (td, 1H), 3.84 (dd, 0.5H), 3.69 (dd, 0.5H), 3.48 (dd, 0.5H), 3.29 (t, 0.5H), 2.79-2.66 (m, 1H), 2.62-2.56 (m, 2H), 2.45 (br s, 1H), 2.13 (s, 3H), 2.04 (d, 3H), 2.03 (d, 3H), 1.96 (s, 3H), 1.82-1.08 (m, 6H).

$^{13}$C NMR (125 MHz, $CDCl_3$) δ=170.5, 170.4, 170.3, 170.2, 169.7, 169.6, 101.8, 101.6, 75.3, 75.2, 71.1, 71.0, 70.8, 70.7, 69.1, 67.2, 61.4, 46.6, 28.7, 28.3, 24.4, 24.3, 20.9, 20.8, 20.7, 20.6.

Measured mass: m/z: [M+H]$^+$=446.2

Preparation of Compound 8:
(Adapted from Thorn-Seshold O., Vargas-Sanchez M., McKeon S., Hasserodt J., *Chem. Comm.* 2012, 48, 6253)

A two-necked round-bottomed flask containing compound 6 (313 mg; 1.1 mmol) was purged three times with vacuum/argon after which anhydrous DCM (3 mL) and dry TEA (300 µL; 2.0 mmol) were added. The resulting suspension was cooled to 0° C. and a solution of triphosgene (990 mg; 3.3 mmol) in dry DCM (4 mL) was added thereto. The resulting reaction mixture was left under agitation at this temperature for one hour after which the volatiles were evaporated using a vacuum pump and collected in a liquid nitrogen trap. While the trapped liquid containing highly toxic phosgene was removed by carefully pouring the mixture of volatiles into a solution of ethanol in DCM (1:1, v/v), the resulting green solid was placed under argon and suspended in dry DCM (4 mL); dry TEA (300 µL; 2.0 mmol) was then added and the mixture cooled to 0° C. before adding dropwise a solution of compound 4 (470 mg; 1.00 mmol) in dry DCM (4 mL). The resulting reaction mixture was left under agitation at this temperature for one hour, then at ambient temperature for 16 hours before being extracted twice with saturated $Na_2CO_3$ solution. The organic phase containing a suspension was filtered through a folded filter and again extracted with deionised water and then a solution of saturated brine. This organic phase was dried ($Na_2SO_4$), filtered and evaporated under reduced pressure to give a beige solid. This reaction crude was purified on two successive silica chromatography columns eluting with a 4:6 ethyl acetate/petroleum ether mixture then 5:5 (v/v) for the first and a gradient of 1/3, 1/2, 4/6, 45/55, 5/5, 55/45 (v/v) of the same eluents for a final yield of compound 8 in the form of a colourless solid (332 mg; 43%) having slight blue fluorescence when placed under a lamp at 365 nm.

$^1$H NMR (500 MHz, $CDCl_3$) δ=10.28-10.16 (m, 1H), 8.25 (s, 1H), 8.01-8.00 (m, 1H), 7.73 (s, 2H), 7.52 (s, 1H), 7.29-7.36 (m, 1H), 5.39 (s, 1H), 5.25-5.17 (m, 1H), 5.01 (d, 1H), 4.64-4.38 (m, containing $H_{anomeric}$ with J=7.9 Hz, 2H), 4.20-4.01 (m, 4H), 3.99-3.90 (m, 1H), 3.60-3.56 (m, 1H), 3.09-2.76 (m, 1H), 2.16 (s, 3H), 2.05 (s, 3H), 1.98 (s, 6H), 1.76-1.65 (m, 6H).

$^{13}$C NMR (125 MHz, $CDCl_3$) δ=170.6, 170.3, 160.6, 153.7, 147.6, 153.3, 133.3, 132.6, 130.6, 129.9, 128.1, 126.1, 125.3, 122.5, 101.9, 101.7, 101.3, 101.2, 71.0, 68.9, 68.6, 67.5, 67.2, 51.4, 50.6, 40.1, 25.2, 20.9, 20.8, 20.8, 19.4, 19.3.

Measured mass: m/z: [M+H]=778.0

Preparation of Compound I.1:

To a solution of compound 8 (150 mg; 0.17 mmol) in anhydrous methanol (3 mL) placed under argon and cooled to 0° C., a solution of sodium methanolate in methanol (1 M; 600 µL; 0.6 mmol) was added dropwise. After a reaction time of one hour at 0° C., mass monitoring indicated the end of the reaction and Dowex® 50×8-100 resin was added until a slightly acid pH was obtained. The reaction medium was then filtered through a sinter filter and evaporated under reduced pressure to yield compound I.1 in the form of a pinkish powder (83 mg; 80%).

$^1$H NMR (500 MHz, CD$_3$OD) δ=8.23-8.21 (m, 1H), 7.89-7.72 (m, 3H), 7.63 (d, 1H), 7.39 (t, 1H), 4.22 (br s, 0.5H), 4.19 (d, H$_{anomeric}$ with J=7.5 Hz, 0.4H), 3.98 (d, H$_{anomeric}$ with J=7.5 Hz, 0.6H), 3.88 (t, 0.5H), 3.82 (br s, 2H), 3.76-3.68 (m, 3H), 3.62-3.57 (m, 2H), 3.51-3.38 (m, 3H), 3.38-3.35 (m, 1H), 3.24-3.17 (m, 0.8H), 2.10-1.76 (m, 5H), 1.33-1.26 (m, 0.6H).

$^{13}$C NMR (125 MHz, DMSO-d$_6$) δ=160.7, 151.3, 150.7, 147.9, 147.0, 134.8, 134.7, 131.4, 131.3, 130.0, 129.5, 129.1, 128.3, 128.2, 124.9, 124.8, 122.3, 103.7, 75.2, 75.1, 73.5, 70.4, 68.1, 68.0, 67.7, 60.2, 59.2, 58.8, 56.8, 46.8, 46.7, 30.0, 27.3, 26.9, 22.9, 22.3, 14.7.

HPLC-MS: column: Phenomenex Polar-RP
eluent: Acetonitrile/Water: 35:65
retention time: 9.42 min
measured masses: m/z: [M+H]$^+$=596.0, [M+Na]=618.0

Example I.4

I.4

Preparation of Compound 5:
(Adapted from Li C., Wang W.-T., *Tetrahedron Lett.* 2002, 43, 3217)

Compound 5 was prepared in similar manner to compound 4, but using 2-pyrrolidinemethanol 3 (787 mg; 7.7 mmol) as reagent to yield compound 5 in the form of an orange solid (730 mg, 33%). The NMR spectra of this compound were highly complex but clearly showed the presence of a single enantiomer (the commercial product 3 was enantiopure) and that the β anomeric bond was indeed formed (7.9 Hz coupling of the anomeric proton of 7.9 Hz, characteristic of this type of bond).

$^1$H NMR (500 MHz, CDCl$_3$) δ=5.39 (d, 1H), 5.20 (dd, 1H), 5.02 (dd, 1H), 4.51 (d, J=7.9, 1H), 4.19-4.13 (m, 2H), 3.94-3.9 (m, 2H), 3.72 (q, 1H), 3.43 (dd, 1H), 3.33-3.27 (m, 1H), 3.03-2.97 (m, 1H), 2.93-2.87 (m, 1H), 2.15 (s, 3H), 2.07 (s, 3H), 2.06 (s, 3H), 1.98 (s, 3H), 1.85-1.73 (m, 4H), 1.45-1.35.

$^{13}$C NMR (125 MHz, CDCl$_3$) δ=170.8, 170.6, 170.4, 170.3, 170.2, 170.1, 101.4, 71.5, 71.1, 70.7, 68.7, 67.2, 61.5, 61.4, 58.8, 46.1, 26.9, 24.2, 23.1, 21.1, 21.1, 20.9, 20.8, 20.8, 20.7.

Measured mass: m/z: [M+H]=432.2

Preparation of Compound 9:
(Adapted from Thorn-Seshold O., Vargas-Sanchez M., McKeon S., Hasserodt J., *Chem. Comm.* 2012, 48, 6253)

Compound 9 was prepared in similar manner to compound 8, but using compound 5 (455 mg; 1.0 mmol) as reagent to yield compound 9 in the form of a white powder (254 mg; 33%) having slight blue fluorescence when placed under a lamp at 365 nm.

$^1$H NMR (500 MHz, CDCl$_3$) δ=10.11 (s, 1H), 8.26 (s, 1H), 8.05 (S, 0.7H), 7.89 (s, 0.3H), 7.34 (s, 2H), 7.52 (dd, 1H), 7.28 (S, 1H), 5.38 (d, 1H), 5.20-5.12 (m, 1H), 5.01-4.97 (m, 1H), 4.47 (d, J=7.9, 1H), 4.12 (t, 2H), 4.01 (br s, 1H), 3.89 (t, 1H), 3.82 (t, 1H), 3.70-3.64 (m, 2H), 3.61-3.55 (m, 1H), 3.52-3.46 (m, 1H), 2.15 (s, 3H), 2.06-1.95 (m, 12H).

$^{13}$C NMR (125 MHz, CDCl$_3$) δ=170.5, 170.4, 170.2, 169.6, 160.9, 152.4, 149.4, 147.6, 135.4, 133.4, 132.4, 131.9, 130.6, 129.7, 127.5, 126.1, 125.3, 122.4, 101.6, 101.3, 71.0, 70.2, 69.4, 68.9, 68.8, 67.1, 61.3, 61.2, 57.87, 57.2, 47.7, 47.6, 28.8, 27.8, 23.8, 24.0, 20.8.

Measured mass: m/z: [M+H]=764.0

Preparation of Compound I.4:

Compound 1.4 was prepared in similar manner to compound 10 but using compound 9 (140 mg; 0.17 mmol) as reagent to yield compound I.4 in the form of a pinkish powder (81 mg; 80%).

$^1$H NMR (500 MHz, CD$_3$OD) δ=8.23-8.21 (m, 1H), 7.89-7.72 (m, 3H), 7.63 (d, 1H), 7.39 (t, 1H), 4.22 (br s, 0.5H), 4.19 (d, H$_{anomeric}$ with J=7.5 Hz, 0.4H), 3.98 (d, H$_{anomeric}$ with J=7.5 Hz, 0.6H), 3.88 (t, 0.5H), 3.82 (br s, 2H), 3.76-3.68 (m, 3H), 3.62-3.57 (m, 2H), 3.51-3.38 (m, 3H), 3.38-3.35 (m, 1H), 3.24-3.17 (m, 0.8H), 2.10-1.76 (m, 5H), 1.33-1.26 (m, 0.6H).

$^{13}$C NMR (125 MHz, DMSO-d$_6$) δ=160.7, 151.3, 150.7, 147.9, 147.0, 134.8, 134.7, 131.4, 131.3, 130.0, 129.5, 129.1, 128.3, 128.2, 124.9, 124.8, 122.3, 103.7, 75.2, 75.1, 73.5, 70.4, 68.1, 68.0, 67.7, 60.2, 59.2, 58.8, 56.8, 46.8, 46.7, 30.0, 27.3, 26.9, 22.9, 22.3, 14.7.

HPLC-MS: column: Phenomenex Polar-RP

Eluent: Acetonitrile/Water: 35:65

Retention time: 9.42 min

Measured masses: m/z: [M+H]=596.0, [M+Na]=618.0

Enzymatic Assays

Probe I.1 was evaluated by incubation with the target enzyme beta-galactosidase (EC 3.2.1.23; <<b-gal>>; commercial) in in vitro medium and in multi-well micro-plates designed for fluorescence readers. The probe was evaluated on the following criteria:

Evidencing of high fluorescence intensity generated by the presence of enzymatic activity (<<on>>);

Evidencing of total absence of fluorescence (<<off>>) in samples not containing the target enzyme (no intrinsic fluorescence);

Evidencing of the absence of any hydrolytic degradation of the probe over time demonstrating the robustness of the probe at pH 7 in an aqueous medium (no false positive signal);

Evidencing of rapid response to the presence of enzymatic activity allowing a maximum signal to be reached rapidly;

Evidencing of the correlation between the measured signal and the concentration of the probe;

Evidencing of strong photo-stability of the generated solid fluorophore under extended irradiation by the fluorescence reader.

The main assays were conducted at 25° C. in solutions buffered at pH 7.4, physiological pH). Assays at 37° C. would have required protection of the wells against early evaporation e.g. by covering with a film which would have caused a strong reduction in the sensitivity of fluorescence measurement. A temperature of 25° C. was therefore preferred.

Preamble:

In the invention when implementing the enzymatic assays, once the minimum concentration allowing triggering of crystal nucleation is reached, there is depositing of a solid fluorophore in a well of a multi-well plate. The time to triggering of nucleation (≥10 min) can be clearly seen in the kinetic curves shown in the Figures.

The following enzymatic assays of probe I.1 were performed in a 96-well microplate in a microplate spectrofluorimeter of Mithras LB 940 type by BERTHOLD TECHNOLOGIES. The excitation wavelength was set at 355 and the detection wavelength at 510 nm, conforming to the spectral properties of dichloro-HPQ.

Figure 1:
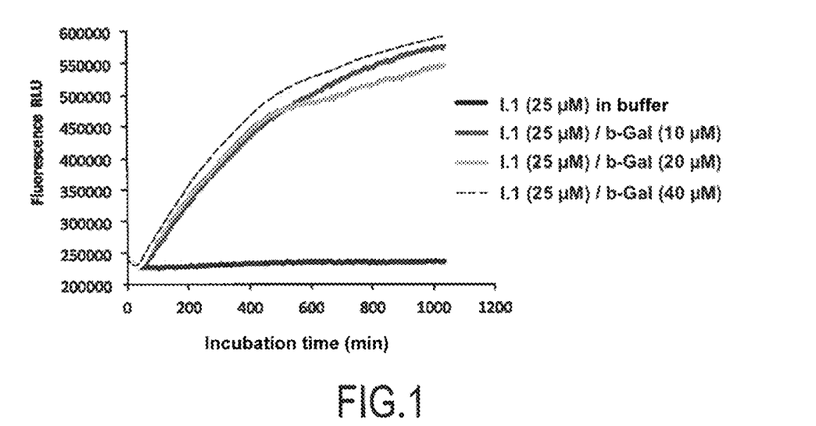
FIG. 1 shows the trend in fluorescence signals (RLU=random luminescence units) caused by contacting compound 1.1 at a fixed concentration (25 μM) with three different concentrations respectively of the b-gal enzyme. A 4$^{th}$ plot corresponds to the negative control, i.e. to the trend in the fluorescence signal of compound I.1 in the absence of enzyme. This curve remains planar thereby demonstrating the total absence of a fluorescence signal when there is no biochemical stimulus: the background signal is therefore not at all modified by the presence of the intact probe. The independency of the signal can also be ascertained in relation to the concentration of target enzyme within the chosen concentration range.
Figure 2:
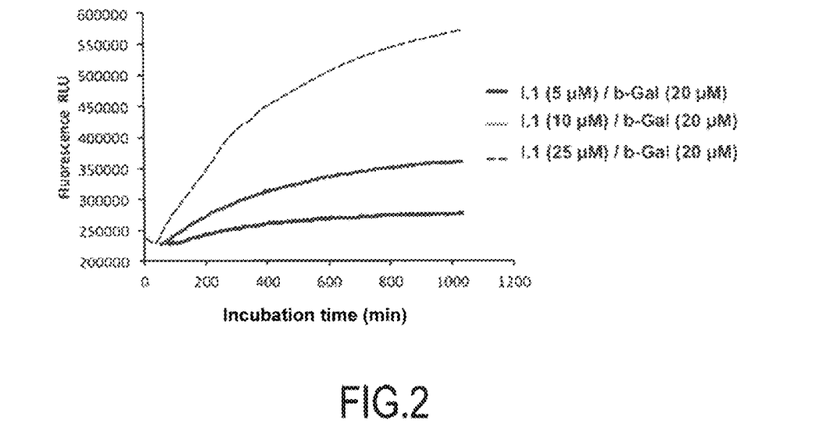
FIG. 2 shows the trend in fluorescence signals (RLU=random luminescence units) caused by contacting the target enzyme b-gal at a fixed concentration (20 μM) with three different concentrations respectively of probe I.1. Strong growth of the signal can be seen with the increase in probe concentration.
Figure 3:
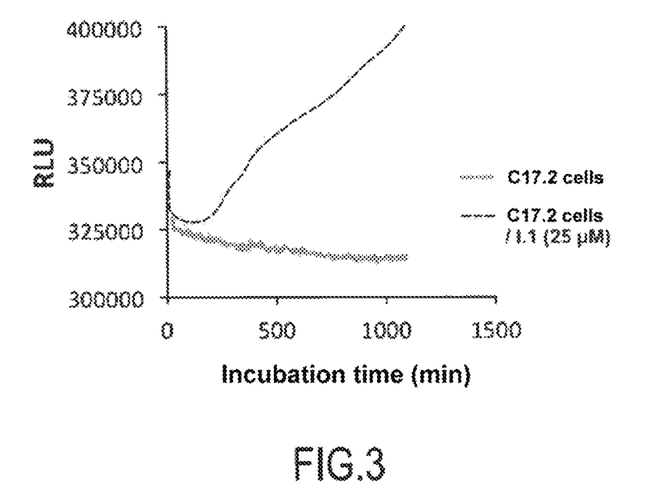
FIG. 3 shows the incubation of probe I.1 (25 μM) with cells of C17.2 type which express the target enzyme b-gal constitutively. The experiment was conducted in a cell culture plate without serum, and the fluorescence signal was measured by the microplate spectrofluorimeter of Mithras LB 940 type by BERTHOLD TECHNOLOGIES. The curve corresponding to the negative control shows the absence of any generation of a fluorescent signal.
Figure 4:
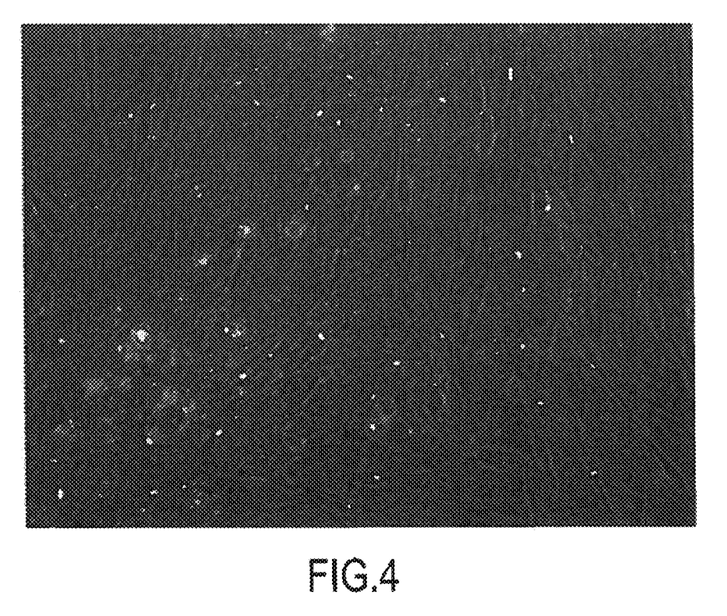
FIG. 4 is a microscope image of the fluorescence of cells expressing b-gal constitutively and which were incubated by probe I.1 at 25 μM for 48 hours in a serum-free medium. Those cells can be clearly identified in which the concentration of converted I.1 has reached a level at which highly fluorescent dichloro-HPQ is precipitated (white spots).

The results obtained are given in FIGS. 1 to 4.

The invention claimed is:

1. A compound of formula (I) which is a substrate of glycosidase:

wherein:
R₀ is a glycosyl group bonded via its anomeric carbon to the oxygen shown in structure of formula (I);
R₁, R₂ and R₃ are defined as follows:
  R₁ is a (C₁-C₄)alkyl or hydrogen, R₂ is a (C₁-C₄)alkyl and R₃ is a (C₁-C₄)alkyl; or
  R₁ is a (C₁-C₄)alkyl or hydrogen; R₂ and R₃ are linked together with the carbon and nitrogen atoms to which they are bonded to form a heterocycle, wherein the heterocycle is optionally substituted by an ammonium, a carboxylate or a sulfonate group which causes an increase in the water-solubility of the substrate;
R₄ is such that HOR₄ is a phenolic fluorophore that exhibits fluorescence due to excited state intramolecular proton transfer (ESIPT) when the substrate is cleaved by a glycosidase, in the form of a mixture of optical isomers in any proportion or in a form enriched with an optical isomer.

2. A compound according to claim 1, wherein R₁=H, and R₂ and R₃ are linked together and form a —CH₂)ₘ— chain, where m=3, 4, or 5.

3. A compound according to claim 1, wherein R₁, R₂, and R₃ are the same, or different, and represent a (C₁-C₄)alkyl group.

4. A compound according to claim 3, wherein R₁=R₂=R₃=—CH₃.

5. A compound according to claim 1, wherein OR₄ is represented by group (C):

wherein:
X₂ is an oxygen atom and X₁ is selected from —NH₂, —OH, —SH, alkyl, aryl, —O-alkyl, —O-phenyl, —NH-alkyl, —NH-phenyl, —S-alkyl or —S-aryl, wherein said alkyl and phenyl groups are substituted or unsubstituted; or X₂ is a nitrogen atom and is then bonded to X₁ which then represents CH, O, S, N or NH to form a substituted or unsubstituted heteroaryl; and represents a substituted, or unsubstituted aryl, or heteroaryl.

6. A compound according to claim 5, wherein:

represents a substituted or unsubstituted group selected from the group consisting of phenyl, and naphthyl;
  wherein X₃ represents S, O, or NR", and R" represents hydrogen or a (C₁-C₄)alkyl group.

7. A compound according to claim 1, wherein OR₄ is selected from formula (A):

wherein:
-T- is —NH—C(O)—, —S—, —O—, —NH—, —N(alkyl)-, or —N(aryl)-;
Ra is hydrogen, or an electron-attracting substituent;

Rb is hydrogen, chlorine, bromine, iodine, fluorine, —OH, —NH$_2$, —NRgRh, —NHRg, or —ORg, wherein Rg and Rh each independently represent a (C$_1$-C$_4$)alkyl group; or Ra and Rb are linked together to form a substituted or unsubstituted hydrocarbon chain of 4 or 5 members that is saturated or unsaturated, and optionally interrupted by one or more heteroatoms selected from N, S and O;

Rc is hydrogen, Br, Cl, I or F;

or OR$_4$ is selected formula (B):

(B)

wherein:

T' is —NH$_2$, —OH, an aryl, (C$_1$-C$_4$)alkyl, —SH, —NHR, —OR, —NRR' or —SR, wherein R and R' are the same or different and represent a (C$_1$-C$_4$)alkyl or aryl;

R'a is hydrogen or an electron-attracting substituent;

R'b is hydrogen, chlorine, bromine, iodine, fluorine, —OH, —NH$_2$, —NR'gR'h or —OR'g, wherein R'g and R'h are the same or different and represent a (C$_1$-C$_4$)alkyl group; or R'a and R'b are linked together to form a substituted or unsubstituted hydrocarbon chain of 4 or 5 members that is saturated or unsaturated, and optionally interrupted by one or more heteroatoms selected from N, S and O.

8. A compound according to claim 7, wherein Ra is an electron-attracting substituent selected from the group consisting of —CN; —COORd, where Rd represents a (C$_1$-C$_4$) alkyl group; —CONReRf, where Re and Rf are the same or different, and represent hydrogen or a (C$_1$-C$_4$)alkyl group; —CF$_3$; 2-oxazolyl; 2-thiazolyl; 2-imidazolyl; 2-benzoimidazolyl; 4-pyrimidinon-2-yl; and quinazolinon-2-yl.

9. A compound according to claim 7, wherein R'a is an electron-attracting substituent selected from the group consisting of —CN; —COOR'd, where R'd represents a (C$_1$-C$_4$) alkyl group; —CONR'eR'f, where R'e and R'f are the same or different and represent hydrogen or (C$_1$-C$_4$-)alkyl group; —CF$_3$; 2-oxazolyl; 2-thiazolyl; 2-imidazolyl; 2-benzoimidazolyl; 4-pyrimidinon-2-yl; and quinazolinon-2-yl.

10. A compound according to claim 1 of formula (IA):

(IA)

wherein:

R$_0$, R$_1$, R$_2$ and R$_3$ are as defined in claim 1, in the form of a mixture of optical isomers in any proportion, or in a form enriched with an optical isomer.

11. A compound according to claim 1, wherein R$_0$ is a mono-glycosyl or poly-glycosyl group.

12. A compound according to claim 1, wherein R$_0$ is a mono-glycosyl group selected from the group consisting of galactosyl, glucosyl, mannosyl, gulosyl, allosyl, altrosyl, idosyl, talosyl, fucosyl, fructosyl, arabinosyl, lyxosyl, ribosyl, xylosyl, glucuronyl, N-acetyl-hexosaminyl, and a polyglycosyl group formed of several of said monoglycosyl groups that are the same or different.

13. A compound according to claim 1, wherein the R$_0$—O bond is cleavable via hydrolysis by the action of a glycosidase selected from the group consisting of N-acetyl-β-galactosaminidase, N-acetyl-β-glucosaminidase, α-amylase, α-arabinofuranosidase, α-arabinosidase, β-cellobiosidase, β-chitobiosidase, α-galactosidase, β-galactosidase, α-glucosidase, β-glucosidase, β-glucuronidase, α-maltosidase, α-mannosidase, β-mannosidase, β-xylosidase, α-D-fucosidase, α-L-fucosidase, 13-L-fucosidase, L-iduronidase, and cellulase.

14. A method for the in vitro or ex vivo detection of the presence of a catalytically active glycosidase, comprising the steps of:

contacting a sample suspected of contained the said glycosidase with a compound according to claim 1 under suitable conditions to allow for the formation of a fluorescent precipitate due to the cleavage of the covalent bond between O and R$_0$, which leads to the cleavage of the covalent bond between —C(O) and OR$_4$ due to the cyclisation of the spacer —OCH$_2$C (R$_1$R$_2$) N(R$_3$) C(O)—; and quantitatively or qualitatively analysing said fluorescent precipitate.

15. The method according to claim 14, wherein the analysis of the fluorescent precipitate comprises:

exposing the fluorescent precipitate to a light source capable of producing light at an absorption wavelength of the fluorescent precipitate; and detecting the resultant fluorescence from the fluorescent precipitate.

16. A method of detecting a glycosidase enzyme in vivo in a mammal, comprising administering the compound of claim 1 to the mammal, and detecting the glycosidase enzyme.

* * * * *